United States Patent
Pike

(10) Patent No.: US 6,224,536 B1
(45) Date of Patent: May 1, 2001

(54) METHOD FOR DELIVERING RADIATION THERAPY TO AN INTRAVASCULAR SITE IN A BODY

(75) Inventor: Kelly Pike, Half Moon Bay, CA (US)

(73) Assignee: Advanced Cardiovascular Systems, Santa Clara, CA (US)

(*) Notice: Subject to any disclaimer, the term of this patent is extended or adjusted under 35 U.S.C. 154(b) by 0 days.

(21) Appl. No.: 09/245,651

(22) Filed: Feb. 8, 1999

(51) Int. Cl.$^7$ ................................................. A61N 5/00
(52) U.S. Cl. ................................................................ 600/3
(58) Field of Search .................................. 600/1–3, 4–8; 606/191, 195, 198

(56) References Cited

U.S. PATENT DOCUMENTS

| | | |
|---|---|---|
| 4,764,394 * | 8/1988 | Conrad .................................. 427/525 |
| 5,126,163 | 6/1992 | Chan . |
| 5,158,548 | 10/1992 | Lau et al. . |
| 5,212,425 | 5/1993 | Goebel et al. . |
| 5,242,399 | 9/1993 | Lau et al. . |
| 5,302,168 | 4/1994 | Hess . |
| 5,342,283 | 8/1994 | Good . |
| 5,344,426 | 9/1994 | Lau et al. . |
| 5,360,401 | 11/1994 | Turnland . |
| 5,374,456 | 12/1994 | Matossian et al. . |
| 5,421,955 | 6/1995 | Lau et al. . |
| 5,503,613 | 4/1996 | Weinberger . |
| 5,514,154 | 5/1996 | Lau et al. . |
| 5,569,295 | 10/1996 | Lam . |
| 5,713,828 | 2/1998 | Coniglione . |
| 5,722,984 | 3/1998 | Fischell et al. . |
| 5,730,698 * | 3/1998 | Fischell et al. ........................... 600/3 |
| 5,849,206 | 12/1998 | Amon . |

FOREIGN PATENT DOCUMENTS

| | | |
|---|---|---|
| 0 688 580 A1 | 6/1994 | (EP) . |
| 0 819 446 | 1/1998 | (EP) . |
| WO 99 02195 | 1/1999 | (WO) . |
| PCT/US00/03172 | 7/2000 | (WO) . |

* cited by examiner

*Primary Examiner*—Max Hindenburg
(74) *Attorney, Agent, or Firm*—Blakely, Sokoloff, Taylor & Zafman LLP

(57) ABSTRACT

An intravascular device such as a stent is placed in a plasma source ion implantation (PSII) chamber wherein a plasma of radioactive ions is introduced to surround the device. A negative potential is applied to the stent to accelerate the ions towards the device and implant them into the surface of the device, thereby rendering the device radioactive. The stent is next deployed intravascularly within a patient's body to maintain the patency of a blood vessel and irradiate the surrounding tissue to prevent the development of restenosis.

25 Claims, 2 Drawing Sheets

METHOD FOR DELIVERING RADIATION THERAPY TO AN INTRAVASCULAR SITE IN A BODY

BACKGROUND OF THE INVENTION

1. Field of the Invention

The present invention relates to a method for delivering radiation therapy to a patient to reduce the likelihood of development of restenosis and intimal hyperplasia after an intravascular procedure such as percutaneous transluminal coronary angioplasty (PTCA), and more particularly to an improved method for safely and economically activating a metallic stent to emit radioactivity after it has been deployed within the patient's vasculature.

2. Description of the Prior Art

In PTCA procedures, a guiding catheter having a preshaped distal tip is introduced percutaneously into the cardiovascular system of a patient and advanced therein until the pre-shaped distal tip is disposed within the aorta, adjacent to the ostium of the desired coronary artery. The guiding catheter is twisted or torqued from the proximal end to turn the distal tip of the guiding catheter so that it can be guided into the coronary ostium. In an over-the-wire dilatation catheter system, a dilatation catheter having a balloon on its distal end and a guide wire slidably disposed within an inner lumen of the dilatation catheter are introduced into and advanced through the guiding catheter to its distal tip. The distal tip of the guide wire usually is manually shaped (i.e., curved) before the guide wire is introduced into the guiding catheter along with the dilatation catheter. The guide wire usually is first advanced out the distal tip of the guiding catheter, into the patient's coronary artery, and torque is applied to the proximal end of the guide wire, which extends out of the patient, to guide the curved or otherwise shaped distal end of the guide wire as the guide wire is advanced within the coronary anatomy until the distal end of the guide wire enters the desired artery. The advancement of the guide wire within the selected artery continues until its distal end crosses the lesion to be dilated. The dilatation catheter then is advanced out of the distal tip of the guiding catheter, over the previously advanced guide wire, until the balloon on the distal extremity of the dilatation catheter is properly positioned across the lesion. Once properly positioned, the dilatation balloon is inflated to a pre-determined size (preferably the same as the normal inner diameter of the artery at that particular location) with radiopaque liquid at relatively high pressures (e.g., 4.052 to 12.16 bars (4–12 atmospheres)) to dilate the stenosed region of the diseased artery. The balloon then is deflated so that the dilatation catheter can be removed from the dilated stenosis and blood flow can resume through the dilated artery.

A common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. It is currently estimated that approximately one third of patients undergoing PTCA procedures develop restenosis within six months. In order to prevent this occurrence and thus obviate the need to perform bypass surgery or subsequent angioplasty procedures, various devices and procedures have been developed for reducing the likelihood of development of restenosis after arterial intervention. For example, an expandable tube (commonly termed a "stent") designed for long term implantation within the body lumen has been utilized to help prevent restenosis. By way of example, several stent devices and stent delivery systems can be found in commonly assigned and commonly owned U.S. Pat. No. 5,158,548 (Lau et al.); U.S. Pat. No. 5,242,399 (Lau et al.); U.S. Pat. No. 5,344,426 (Lau et al.); U.S. Pat. No. 5,421,955 (Lau et al.); U.S. Pat. No. 5,514,154 (Lau et al.); U.S. Pat. No. 5,569,295 (Lam); and U.S. Pat. No. 5,360,401 (Tumlund et al.), which are hereby incorporated herein in their entirety by reference thereto.

More recent devices and procedures for preventing restenosis after arterial intervention employ the use of a radiation source to minimize or destroy proliferating cells which are thought to be a major factor in restenosis development. Balloon catheters have been suggested as a means to deliver and maintain the radiation source in the area where arterial intervention has taken place, exposing the area to a sufficient radiation dose to abate cell proliferation. Two such devices and methods are described in U.S. Pat. No. 5,302,168 (Hess) and U.S. Pat. No. 5,503,613 (Weinberger). Other devices and methods which utilize radiation treatment delivered by an intravascular catheter are disclosed in commonly assigned and commonly owned co-pending U.S. Ser. No. 08/654,698, filed May 29, 1996, entitled Radiation-Emitting Flow-Through Temporary Stent, which is hereby incorporated herein in its entirety by reference thereto.

Another medical device for the treatment of a body lumen by radiation is disclosed in European Patent App. No. 0 688 580 A1 (Schneider). In the Schneider device, the balloon catheter includes a lumen that extends from a proximal opening to an area near the distal end of the catheter, where it dead ends. This lumen, known as a "blind" or "dead end" lumen, is intended to carry a radioactive tipped source wire that slides into the lumen once the catheter is in place in the artery or body lumen. When the source wire is positioned, the radioactive section at the distal tip lies near the dead end to provide radiation to the body lumen.

Another procedure employed to deliver a radiation source to a vessel is disclosed in U.S. Pat. No. 5,503,613 (Weinberger), wherein a catheter is provided with two inner lumens. One lumen accepts a guide wire for sliding into the body lumen. The other lumen is a blind lumen and receives a radiation dose delivery wire manipulated remotely by a computer controlled afterloader. After the catheter has been positioned with its distal end lying just past the stenosed area, the radiation dose delivery wire is inserted into the open end of the blind lumen and advanced to the dead end where it delivers a radiation dose to the affected tissue. This method necessitates a rather large catheter cross section to accommodate both lumens, which can complicate the insertion of the catheter in narrow, tortuous arteries. Another method bypasses this problem by employing an over-the-wire catheter to treat the stenosed region, then withdrawing the guide wire and inserting the radiation dose delivery wire in its place. Unfortunately, with this latter device, the radiation source wire will be exposed to blood, requiring sterilization if reuse is contemplated, or disposal after one use, which is costly and presents radioactive waste disposal issues.

The use of nuclear radiation to prevent restenosis represents a significant improvement in the safety and success rate of PTCA and percutaneous transluminal angioplasty (PTA) procedures. However, a few attendant factors give rise to special considerations that must be addressed to successfully employ this method. In particular, withdrawing the guide wire is disfavored by physicians because it results in a more complex and lengthy procedure, thereby increasing the risk of complications. Furthermore, if the radiation source delivery wire comes in direct contact with the patient's blood, it can cause blood contamination requiring that the radiation wire be sterilized before it is retracted into the afterloader and used on another patient. In addition, the salts and other chemical compounds found in blood may adversely impact the radiation source delivery wire and shorten its useful life.

Another consideration peculiar to intraluminal radiation therapy is that the radiation source must be located centrally within the body lumen being treated to assure uniform delivery of the radiation dose to the entire target area. Typically the radioactive sources employed are gamma ray emitters, and point source gamma rays attenuate inversely with the square of the distance traveled. If the radiation dose delivery wire lies closer to one side of the lumen or at an angle to it, the radiation dose delivered will be nonuniform along the entire length of the target area and some areas can receive appreciably larger doses than others. Achieving such precise spatial alignment of the radiation dose delivery wire is difficult in practice. Although this problem is not encountered when the radiation source is embedded in the tip of the catheter, which is usually centered within the lumen by the inflated balloon, the use of catheters to deliver the radiation dose can result in increased radiation doses being delivered to the body lumens leading to the stenosed area due to the longer insertion time required for catheters. In addition, repeated insertion and withdrawal of catheters can cause additional damage to vascular tissue due to their relatively large cross section.

A group of devices that address most of these problems comprises permanently implantable elements. Fischell, for example, discloses in his U.S. Pat. No. 5,722,984 an intravascular stent with a single layered coating of an antithrombogenic coating that incorporates radioisotopes such as phosphorus 32. The preferred coating is the organic compound phosphorylcholine, the phosphate groups of which contain the radioisotopes. In U.S. Pat. No. 5,713,828, Coniglione discloses a double-walled tubular brachytherapy device with an inner tubular element with an outer surface that incorporates radioactive material. Methods disclosed for incorporating the radioactive material onto this surface include plating, the application of an organic coating such as through solvent evaporation, chemical polymerization, or plastic molding, and neutron irradiation of transmutable, non-radioactive isotopes. The device is intended to be implanted interstitially at the site of a tumor and secured therein with suture material, rigid rods, and other typical surgical connecting members. And in U.S. Pat. No. 5,342,283, Good discloses multilayered devices such as microspheres, ribbons, and wires that include a layer incorporating radioactive materials implanted therein through a host of methods, including plasma sputtering, laser ablation, cathodic arc plasma deposition, ion beam sputtering, ion plating, and neutron irradiation. The devices can be implanted individually or incorporated into other devices such as fabrics.

The permanently implantable radioactive devices disclosed by these patents are advantageous because they can provide much lower doses of radiation upon initial implantation into the patient as compared to temporary devices due to the significantly longer treatment periods over which they emit radiation, and are therefore less likely to affect healthy tissue surrounding the treatment target area. However, the methods disclosed for rendering these devices radioactive suffer from some common shortcomings, most notably the need to prepare the device at a site removed from the hospital such as nuclear reactors for neutron irradiation. This necessitates that the devices be prepared so as to emit relatively high initial levels of radiation in order to account for the natural decay of radioisotopes and ensure that the device is emitting the required level of radiation by the time it is implanted into the patient, which may be days or weeks after the device has been rendered radioactive. This in turn poses increased risks to attending personnel, imposes strict safety measures upon the storage and handling of the devices, and results in much higher cost to the patient. Furthermore, the chemical deposition of radioactive material renders such material more vulnerable to leaching out of the device, and therefore require additional layers to protect the radioactive material from contact with the patient's tissue and blood, thereby further increasing the complexity, size, and cost of these devices, as well as reducing their efficacy due to the radiation shielding effects of such additional layers. The various plasma deposition methods disclosed by Good, on the other hand, require rather elaborate and expensive facilities, as well as lengthy processing times due to the inability of the listed processes to simultaneously implant ions over an object's entire surface; rather, these processes function by extracting ions from a plasma and accelerating them into a beam that is impacted into a typically very small area on the surface of the target. These methods are therefore rather complex and expensive to practice due to the need to manipulate the target object and/or the ion beam in order to adequately and uniformly cover the surface of the target, require relatively longer processing times, and are not particularly well suited to treating irregularly shaped or curved targets.

In light of the above, it becomes apparent that there continues to be a need for a method of delivering radiation therapy to an intravascular area within a patient's body with a device that will emit low levels of radiation over a prolonged period of time and that is safe to handle, and simple and inexpensive to manufacture.

SUMMARY OF THE INVENTION

The present invention addresses the above mentioned needs by providing a method for implanting radioactive material into a stent immediately prior to deploying the stent within a patient's vasculature, thereby reducing the risks associated with storing and handling the stent. The method comprises the use of a plasma source ion implantation (PSII) chamber to create a plasma of radioactive material ions which surround the stent or other object to be implanted with radioactive material that has been placed therein. A negative voltage is applied to the stent to create an electric field between the chamber walls and the stent, thereby accelerating the ions towards the stent and implanting them into the surface of the stent. Because the stent is surrounded by a cloud of the plasma ions that are simultaneously accelerated towards the stent, all exposed surfaces of the stent are simultaneously implanted with such ions, thereby reducing the process times and equipment complexity and cost.

The method of the present invention may also be practiced upon a stent that is mounted upon a balloon catheter, wherein the entire catheter and stent assembly is placed within the PSII chamber and exposed to the radioactive material ion plasma. In addition, other surgical devices such as guide wires and grafts may also be activated by the method of the present invention.

DETAILED DESCRIPTION OF THE PREFERRED EMBODIMENTS

In the preferred embodiment, the method of the present invention entails, in its most basic form, the implantation of radioactive material into the surface of a stent prior to deploying the stent within a patient's vasculature, thereby emitting radiation to the surrounding tissues and preventing the formation of restenosis. The method by which the radioactive material is implanted into the stent is plasma source ion implantation (PSII). As described in U.S. Pat. No. 4,764,394 to Conrad, U.S. Pat. No. 5,126,163 to Chan, U.S. Pat. No. 5,374,456 to Matossian, and U.S. Pat. No. 5,212,425 to Goebel, the disclosures of which are incorporated herein in their entirety by reference thereto, the basic PSII process uses a plasma chamber to generate a plasma of the material to be implanted and applies a large voltage differential between the walls of the chamber and the target object, in the present case the stent, to accelerate the ions towards the stent and drive them into the surface of the stent.

Figure 1:
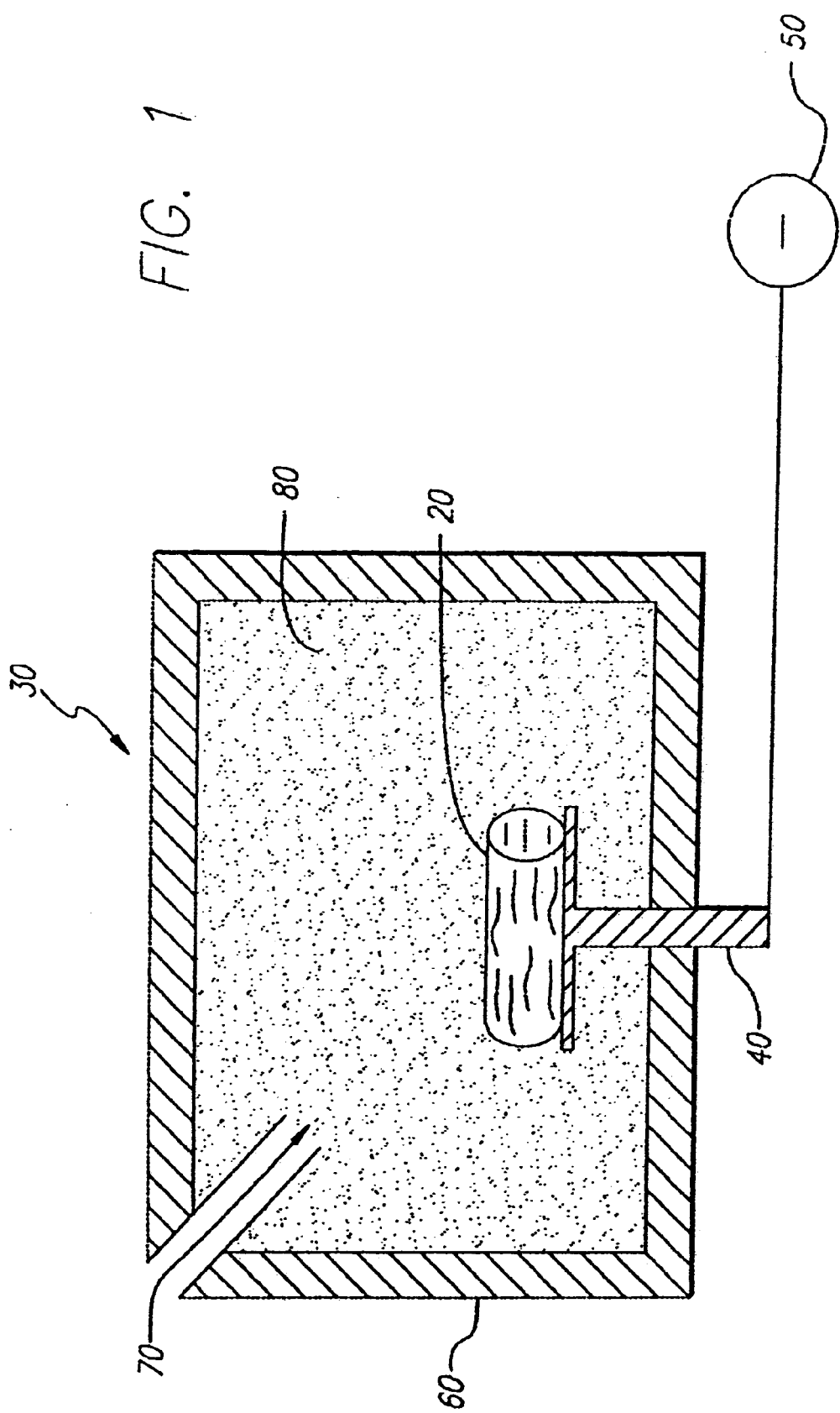
FIG. 1 depicts a stent being treated in a plasma source ion implantation chamber, according to the method of the present invention.

With reference to FIG. 1, as a first step, the target object, i.e., stent 20, is placed within PSII chamber 30. The chamber is equipped with electrode 40 in contact with negative voltage source 50 that may be located external of the chamber. The chamber is further formed with conductive walls 60 so as to enable the creation of an electric field between the walls of the chamber and the electrode and any conductive objects in contact with the electrode through the application of a negative voltage to the electrode or, alternatively, a positive voltage to the chamber walls. The chamber is then sealed and a vacuum is created to remove all air from within and thus ensure that no impurities are present in the plasma that is subsequently introduced. The next step entails creating a plasma of radioactive material ions.

With continued reference to FIG. 1, the plasma may be created by introducing the radioactive material in gas or vapor form and then exposing the material to ionizing radiation, such as electrons from a heated filament electron source or electromagnetic radiation, to create a plasma of radioactive material ions. Alternatively, an arc source may be utilized to create fully ionized radioactive metal plasma 70 and inject the plasma into chamber 30. Once formed and introduced into the chamber, plasma 70 forms ion cloud 80 that disperses throughout the chamber and surrounds both the inside and the outside tubular surfaces of stent 20 placed within.

Referring still to FIG. 1, in the next step negative voltage generator 50 is connected to electrode 40 so as to create a voltage potential difference between chamber walls 60 and stent 20 in electrical contact with the electrode, thus setting up an electric field emanating from the chamber walls towards the stent. The electric field will instantly accelerate radioactive plasma ions 80 towards the stent and implant them into all surfaces of the stent that are exposed to the plasma cloud. The stent will now be emanating radiation from these surfaces due to the radioactive decay of the radioactive ions implanted therein.

The amount of radiation emitted by the stent will be a function of the half-life of the ions and the amount of such ions implanted therein. While there are numerous radioactive sources available for use with the present invention, the following radioisotopes are preferred: Iridium 192; Sodium 22; Scandium 46; Manganese 54; Yttrium 88; Cerium 139; Cerium 141; Strontium 85; Cobalt 57; Cobalt 60; Cesium 134; Palladium 103; Gold 198; Niobium 95; Mercury 203; Iodine 125; and Iodine 131. While gamma radiation is preferred for use with the present invention, beta radiation also is contemplated. Although beta radiation typically does not penetrate as well as gamma radiation through matter, it may be employed in the present application because the process of the present invention implants the ions into the surface of the stent and in close proximity to the patient's tissue when the stent is deployed intravascularly, and thus the self shielding action of the stent's structure will not have a significant impact upon the level of radiation emitted by the stent.

Figure 2:
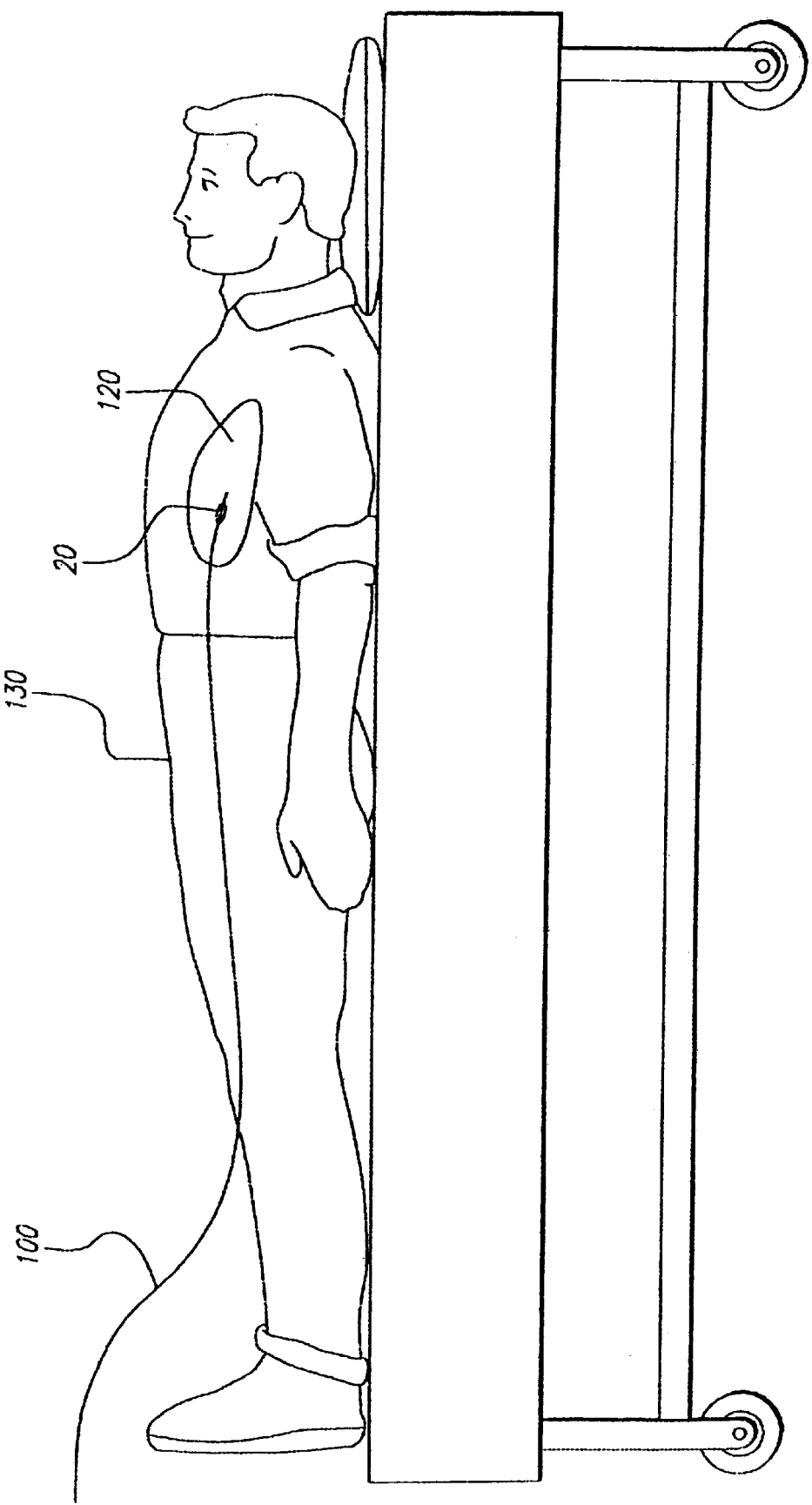
FIG. 2 shows the stent depicted in FIG. 1 deployed at an intravascular site within a patient's body.

With reference now to FIG. 2, after the desired amount of radioactive ions have been implanted in stent 20, the stent is removed from the plasma chamber, mounted upon balloon catheter 100, and deployed in patient's body 130 at desired intravascular site 120 where the lesion occurred and the PTCA procedure must be performed, as known in the art and detailed in the patents referenced elsewhere in the disclosure. In an alternative method according to the present invention, the stent may be mounted upon a balloon catheter prior to being implanted with radioactive ions, and placed in the plasma chamber for treatment as detailed previously. Such an approach will eliminate handling of the stent by personnel to mount the radioactive stent upon the catheter, and thus reduce the risk of inadvertent radiation exposure. Because the catheter and balloon are typically constructed of non-conductive materials such as plastic, the application of a negative voltage to the stent will not affect the catheter and thus will not result in ions being implanted into the catheter. In addition, the balloon will also prevent the plasma cloud generated within the plasma chamber from diffusing into the interior of the stent, and will thus ensure that the interior surface of the stent is not implanted with radioactive ions. This may be advantageous because the interior surface of the stent is in contact with the patient's blood when deployed intravascularly in the patient's body, and radiation emitting from this surface may irradiate the blood, thereby resulting in radiation being delivered at other intravascular sites within the patient's body.

As detailed above, the method of the present invention allows the preparation of a stent for radiation therapy with relatively simple and economical equipment, due to the ability to simultaneously implant radioactive material in all exposed surfaces of the stent. Complex equipment for manipulating the stent or the ion beam, as required by previously utilized methods of ion implantation, are not required by the process of the present invention, thereby resulting in simpler equipment and shorter implantation times. A stent can therefore now be activated just prior to being implanted in a patient's body, eliminating the uncertainty associated with the limited shelf life of radioactive devices caused by their constant radioactive decay action.

Furthermore, the implantation process ensures that the radioactive ions penetrate into the surface of the stent and thus become part of the stent's molecular structure, as opposed to simply creating a chemically bonded layer overlaying the surface of the stent. As a result, the radioactive ions are much less likely to leach into and contaminate the tissue or blood of the patient.

It will therefore be apparent from the foregoing that while particular forms of the invention have been illustrated and described, various modifications can be made without departing from the spirit and scope of the invention. Thus, the method of the present invention may also be used to activate other surgical devices including, but not limited to, guide wires, grafts, and prostheses. Accordingly, it is not intended that the invention be limited, except as by the appended claims.

What is claimed is:

1. A method comprising:

providing a catheter having an expandable member adjacent a distal end thereof;

providing a radially expandable and permanently deformable intravascular stent;

providing a plasma ion implantation chamber;

loading a preselected amount of a preselected radioactive material into the chamber;

mounting the stent over the expandable member;

placing the stent and catheter in the chamber;

operating the chamber for a preselected length of time to create a plasma of radioactive material ions and implant the ions into the stent to impart a preselected level of radioactivity to the stent;

removing the catheter and stent from the chamber;

introducing the catheter into a patient's vasculature the plasma ion implantation chamber being located proximate to a site where the catheter is introduced into the patient's vasculature;

advancing the catheter to position the stent adjacent to the target site;

inflating the expandable member to expand the stent radially outwardly against the vascular wall and embed the stent into the vascular wall;

deflating the expandable member; and withdrawing the catheter from within the patient's vasculature to implant the stent within the patient to maintain vessel patency and irradiate the vascular wall to inhibit cell growth at the target site.

2. A method as in claim 1, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198, and mercury 203.

3. A method as in claim 1, wherein the radioactive material is selected from the group of materials consisting of alpha-, beta-, and gamma-emitting materials.

4. A method comprising:

providing a radially expandable and permanently deformable intravascular stent;

providing a plasma ion implantation chamber;

loading a preselected amount of a preselected radioactive material into the chamber;

placing the stent in the chamber;

operating the chamber for a preselected length of time to create a plasma of radioactive material ions and implant the ions into the stent to impart a preselected level of radioactivity to the stent;

providing a catheter having an expandable member adjacent a distal end thereof, mounting the stent over the expandable member of the catheter;

introducing the catheter into the patient's vasculature, the plasma ion implantation chamber being located proximate to a site where the catheter is introduced into the patient's vasculature;

advancing the catheter to position the stent adjacent to the target site;

inflating the expandable member to expand the stent radially outwardly against the vascular wall and embed the stent into the vascular wall;

deflating the expandable member; and withdrawing the catheter from within the patient's vasculature to leave the stent implanted within the patient to maintain vessel patency and irradiate the vascular wall to inhibit cell growth at the target site.

5. A method as in claim 4, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198, and mercury 203.

6. A method as in claim 4, wherein the radioactive material is selected from the group of materials consisting of alpha-, beta-, and gamma-emitting materials.

7. A method comprising:

providing a plasma ion implantation chamber;

loading a preselected amount of a preselected radioactive material into the chamber;

placing a stent in the chamber; and operating the chamber for a preselected length of time to create a plasma of radioactive material ions and implant a preselected amount of the ions into the stent to impart a preselected level of radioactivity to the stent, the operating being performed immediately prior to a time when the stent is deployed within a patient's vasculature.

8. A method as in claim 7, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198, and mercury 203.

9. A method as in claim 7, wherein the radioactive material is selected from the group of materials consisting of alpha-, beta-, and gamma-emitting materials.

10. A method comprising:

providing a plasma ion implantation chamber;

loading a preselected amount of a preselected radioactive material into the chamber;

placing a stent in the chamber; and operating the chamber to generate a plasma of radioactive material ions and implant the ions in the stent, the plasma ion implantation chamber being located within a vicinity of a site where the stent is to be deployed within a vasculature of a patient.

11. A method as in claim 10, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198 and mercury 203.

12. A method as in claim 10, wherein the radioactive material is selected from the group of materials consisting of alpha-, beta-, and gamma-emitting materials.

13. A method comprising:

providing a plasma chamber;

placing a stent in the plasma chamber;

applying an energy source to a preselected radioactive material to generate a plasma of radioactive material ions;

introducing the plasma into the chamber to surround the stent; and applying a voltage potential to the stent relative to the chamber to create an electric field between the chamber and the stent to accelerate the radioactive material ions towards the stent and implant the ions therein, the applying a voltage potential being performed at an ion implantation time substantially close to a time when the stent is deployed within a patient's vasculature.

14. A method as in claim 13, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198, and mercury 203.

15. A method as in claim 13, wherein the radioactive material is selected from the group of materials consisting of alpha-, beta-, and gamma-emitting materials.

16. A method comprising:

providing an intravascular device;

providing a plasma chamber having electrically conductive walls;

placing the device in the plasma chamber;

applying an energy source to a preselected radioactive material to create a plasma of radioactive material ions;

introducing a preselected amount of the plasma into the chamber to surround the device;

applying a voltage potential to the device relative to the chamber walls to create an electric field emanating from the chamber walls towards the device to accelerate the radioactive material ions towards the device and implant the ions therein to impart a preselected level of radioactivity to the device; and deploying the device at a preselected intravascular site within the patient's body to irradiate the patient's body tissue, the applying a voltage potential being performed immediately prior to deploying the device at a preselected site within the patient's body.

17. A method as in claim 16, wherein the intravascular device is a stent.

18. A method as in claim 17, wherein the step of deploying the stent comprises the steps of:

providing a catheter having an expandable member adjacent a distal end thereof;

mounting the stent over the expandable member;

percutaneously introducing the catheter into the patient's vasculature;

advancing the catheter to position the stent adjacent to the preselected intravascular site;

inflating the expandable member to expand the stent radially outwardly against the vascular wall;

deflating the expandable member; and withdrawing the catheter from within the patient's vasculature to leave the stent implanted within the patient to irradiate the vascular wall.

19. A method as in claim 18, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198, and mercury 203.

20. A method as in claim 18, wherein the radioactive material is selected from the group of materials consisting of alpha-, beta-, and gamma-emitting materials.

21. A method comprising:

providing an intravascular device;

providing a plasma ion implantation chamber;

loading a preselected amount of a preselected radioactive material into the chamber;

placing the device in the chamber;

operating the chamber to generate a plasma of radioactive material ions and implant the ions in the device; and deploying the device at a preselected intravascular site within the patient's body, the plasma ion implantation chamber being located proximate to a site where the device is deployed at the preselected intravascular site within the patient's body.

22. A method as in claim 21, wherein the intravascular device is a stent.

23. A method as in claim 22, wherein the step of deploying the stent comprises the steps of: providing a catheter having an expandable member adjacent a distal end thereof;

mounting the stent over the expandable member;

percutaneously introducing the catheter into the patient's vasculature;

advancing the catheter to position the stent adjacent to the preselected intravascular site;

inflating the expandable member to expand the stent radially outwardly against the vascular wall;

deflating the expandable member; and withdrawing the catheter from within the patient's vasculature to leave the stent implanted within the patient to irradiate the vascular wall.

24. A method as in claim 23, wherein the radioactive material is selected from the group of materials consisting of sodium 22, phosphorus 32, scandium 46, vanadium 48, manganese 54, cobalt 57, cobalt 60, strontium 85, yttrium 88, niobium 95, palladium 103, iodine 125, iodine 131, cesium 134, cerium 139, cerium 141, iridium 192, gold 198, and mercury 203.

25. A method as in claim 23, wherein the radioactive material is selected from the group of materials consisting of alpha-, beta-, and gamma-emitting materials.

* * * * *

UNITED STATES PATENT AND TRADEMARK OFFICE
CERTIFICATE OF CORRECTION

PATENT NO. : 6,224,536 B1
DATED : May 1, 2001
INVENTOR(S) : Kelly Pike

Page 1 of 1

It is certified that error appears in the above-identified patent and that said Letters Patent is hereby corrected as shown below:

<u>Column 2,</u>
Line 7, "Tumlund" should read -- Turnland --.

<u>Column 7,</u>
Line 20, "vasculature" should read -- vasculature, --.

Signed and Sealed this

Twelfth Day of February, 2002

Attest:

JAMES E. ROGAN
Attesting Officer     Director of the United States Patent and Trademark Office